United States Patent [19]

Suzuki et al.

[11] Patent Number: 5,200,540

[45] Date of Patent: Apr. 6, 1993

[54] REFINING PROCESS OF ORGANIC TIN (IV) POLYHALIDES

[75] Inventors: Yasuyuki Suzuki; Yuji Watanabe; Toshinao Fujita; Naruo Den, all of Tokyo, Japan

[73] Assignee: Koriyama Kasei Co., Ltd., Tokyo, Japan

[21] Appl. No.: 721,560

[22] PCT Filed: Dec. 25, 1990

[86] PCT No.: PCT/JP90/01687

§ 371 Date: Aug. 2, 1991

§ 102(e) Date: Aug. 2, 1991

[87] PCT Pub. No.: WO91/09862

PCT Pub. Date: Jul. 11, 1991

[30] Foreign Application Priority Data

Dec. 28, 1989 [JP] Japan .................................. 1-341188

[51] Int. Cl.$^5$ ................................................ C07F 7/22
[52] U.S. Cl. ........................................................ 556/87
[58] Field of Search ........................................... 556/87

[56] References Cited

FOREIGN PATENT DOCUMENTS 51-46092 12/1976 Japan .
52-41246 10/1977 Japan .
59-21873 5/1984 Japan .

*Primary Examiner*—Arthur C. Prescott
*Attorney, Agent, or Firm*—Joseph C. Mason, Jr.; Ronald E. Smith; George B. Oujevolk

[57] ABSTRACT

It is possible to eliminate organic tin(IV) monohalide from organic tin(IV) polyhalide containing the monohalide so that it can not be detected in sensitivity of ordinary gas chromatography by treating with hydrochloric acid, hydrogen chloride or chlorine.

9 Claims, No Drawings

REFINING PROCESS OF ORGANIC TIN (IV) POLYHALIDES

BACKGROUND OF THE INVENTION

1. Field of Invention

This invention relates, generally, to process for producing organic tetravalent tin polyhalide. More particularly, it relates to a method for refining a mixture of tin halides to obtain a higher yield of the desirable tin polyhalides. The organic tetravalent tin polyhalides are useful as starting materials as a stabilizer for polyvinyl polymers, as polymerization catalyst for the production of polyurethane, and as a builder of a coating film of tin oxide on glass, ceramics, and metals.

2. Description Of Related Art

The commonly know aluminum process in which stannic chloride reacts with alkyl aluminum, the commonly known Grignard Process in which the Grignard regent reacts with stannic chloride, and the commonly known Direct Process in which achyliodide directly reacts with metallic tin have been known as the prior art production methods for producing organic tetravalent tin polyhalides, that is the tin compound whose valence is 4, rather that 2. In both the Aluminum Process and the Grignard Process the corresponding chlorides are formed as intermediate compounds, and in the Direct Process the corresponding iodide is also formed as a intermediate.

For example, dialkyl tin dichloride, one of the polyhalides which can be synthesized by Alkyl Aluminum or Grignard process via tetraalkyl tin (IV) as an intermediate, is disproportionately reacted with equimolecular stannic chloride. Dialkyl tin (IV) diiodide can be synthesized by the Direct Method in which alkyl iodide and metallic tin are reacted with metallic magnesium and alcohol as a catalyst. However, the dialkyl tin (IV) dihalide synthesized by these methods always contains significant amounts of trialkyl tin monohalide and monoalkyl tin trihalide as by-products.

Therefore, it is desirable to eliminate organic tin monohalides from its corresponding polyhalides because it is well known that organic tin monohalides commonly higher toxic than its corresponding polyhalides.

It may be possible to reduce the organic tin monohalide contained in organic tin polyhalide by addition and heating treatment with excess anhydrous stannic chloride for the monohalide and, as a catalyzer, aluminum chloride. However, this process is very expensive and difficult, because of its non-selectivity of the reaction and the disposal requirement for hydroxides formed from stannic chloride involved in the main reaction and from aluminum chloride. Additionally, the monohalide is difficult to eliminate from monoalkyl tin polyhalide by distillation because the boiling point is too close in each other. There are no prior methods reported to eliminate economically a small content of trialkyl tetravalent tin monohalide from monoalkyl tetravalent tin trihalide and dialkyl tetravalent tin dihalide which are similarly synthesized.

Although a decomposition reaction from organic tin monohalide to the polyhalide by hydrochloric acid or chlorine was described in Metal-Organic Compound, item 208 or Chemical Review Vol. 60, item 483, no example to eliminate organic tin monohalide in the polyhalide is shown.

3. Summary of the Invention

This invention relates to a process of treating organic tetravalent tin polyhalide which contains organic tetravalent tin monohalide with hydrochloric acid, hydrogen chloride or chlorine for refining organic tin polyhalide, to selectively decompose and transform organic tetravalent tin monohalide to organic tetravalent tin polyhalide. Furthermore, the reaction efficiency of the present invention can be remarkably improved by the addition of Lewis acid.

Illustrative equations for the reaction between organic tin monohalide and hydrochloric acid, hydrogen chloride or chlorine in this invention are as follows:

1) $R_3SnX + HCl \rightarrow R_2SnXCl + RH$ 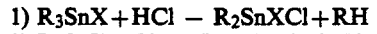
2) $R_3SnX + Cl_2 \rightarrow R_2SnXCl + RCl$ 

wherein, R=alkyl or phenyl, and X=chlorine, bromine, or iodine. As shown, organic tetravalent tin dihalides and organic tetravalent tin trihalides are co-produced with organic tetravalent tin polyhalides in the invention.

Dibutyl tin dichloride, dibutyl tin diiodide, di-butyl tin dibromide, dioctyl tin dichloride, dioctyl tin diiodide, dioctyl tin dibromide, diphenyl tin dichloride and diphenyl tin diiodide can be given as the examples of organic tetravalent tin dihalides. Butyl tin trichloride, butyl tin triiodide, butyl tin bromide, octyl tin trichloride and octyl tin triiodide can be also given as the examples of organic tetravalent tin trihalides. Organic tin monohalide in the invention is defined as the corresponding monohalide to each dihalide or trihalide previously given; then, tributyl tin monochloride, tributyl tin monoiodide, tributyl tin monobromide, trioctyl tin monochloride, trioctyl tin monoiodide, trioctyl tin monobromide, triphenyl tin monochloride and triphenyl tin monoiodide can be given as the examples of the organic tetravalent tin monohalide.

Concentration of hydrochloric acid used in the inventive process is higher than 20%; preferably about 35% is desirable. Either dried or wet hydrogen chloride gas or chlorine can also be usefully applied.

Proper conditions for the method of this invention is a temperature which is dependent upon the type of organic tin polyhalide. The higher temperature results in higher efficiency, but due to undesirable side reaction, such as organic tin dihalide decomposes to organic tin trihalide at temperatures beyond 250° C. Therefore, it is preferable to use a temperature between 100–200° C. Quantity of reacted hydrochloric acid, hydrogen chloride or chlorine depends upon the type of treated organic tin polyhalides. Thus, about 1–100 times on the molar basis of the organic tin monohalide is a reasonable ratio, preferably 20–50 times molar. Most of hydrochloric acid, hydrogen chloride or chlorine can be recovered, so its net quantity consumed through the reaction is very slight.

According to the inventive method, the reaction procedure comprises organic tin polyhalide which is mixed already with hydrochloric acid is slowly heated under stirring conditions or the latter is dropped into the former already heated. In this case higher contact efficiency of the stirring is desirable. In the reaction with hydrogen chloride or chlorine, it is introduced as a gas into already heated organic tin polyhalide admixture which is to be refined. In this case the higher contact of the gas with the reacting solution is also desirable; therefore, location at where the gas is introduced is more desirable to be inside of liquid organic tin polyhalide mixture than at its surface. Contact time is preferably 2 to 3 hours; 1 to 2 hours; and 10 minutes to 1 hour in the case of hydrochloric acid, hydrogen chloride or chlorine, respectively. The content of organic tin monohalide in the polyhalides is reduced to be less than 10 ppm by the method of this invention.

A catalyst is not necessary in the practice of this process, but the reaction is effectively accelerated by a slight addition of Lewis acid. Most of all Lewis acid widely known are useful, for example $AlCl_3$, $AlBr_3$, $AlI_3$, $GaBr_3$, $GaCl_3$, $FeCl_3$, $SbCl_5$, $SnCl_4$, $SnI_4$, $ZnCl_4$, $BCl_3$, $BF_3$, and $ZnCl_3$; the most preferable of these is $AlCl_3$ because of its lower expense and higher effectiveness.

As a further embodiment of this invention the refined organic tetravalent tin polyhalide is successively hydrolyzed to organic tin oxide, which is further less contaminated by organic tin monohalide. The hydrolysis is carried out according to a method, for example, described in Japanese Pat. No. Sho 61-291592 (1986).

Thus, the disadvantages of the prior art are overcome by the inventive method which comprises a method for producing an organic tetravalent tin polyhalide which comprises contacting an admixture of organic tetravalent tin polyhalide and organic tetravalent tin monohalide with hydrochloric acid, hydrogen chloride or chlorine in an amount and under condition sufficient to convert the organic tetravalent tin monohalide to organic tetravalent tin polyhalide. A further embodiment of the invention includes a method for producing an organic tetravalent tin polyhalide which comprises contacting an admixture of an organic tetravalent tin polyhalide of the formula $$R_2Sn X_2 \quad (A)$$ 

wherein
R is alkyl or phenyl, and,
X is chlorine, bromine, or iodine
and an organic tetravalent tin monohalide of the formula $$R_3Sn X \quad (B)$$ 

wherein
R is alkyl or phenyl, and,
X is chlorine, bromine, or iodine
with hydrochloric acid, hydrogen chloride, or chlorine in an amount from 1 to 100 moles per mole of (B) and at a temperature from 100° to 250° C. sufficient to convert (B) to (A). A specific embodiment of this invention comprises a method for producing an organic tetravalent tin polyhalide which comprises (a) the process of reacting a tetravalent tin halide with organoaluminum, a Grignard agent, or the process of reacting metallic tetravalent tin with an organohalide, thereby producing a reaction product comprising an organic tetravalent tin polyhalide and by-product organic tetravalent tin monohalide, such process does not include the removal of the by-product, (b) contacting the reaction product with hydrochloric acid, hydrogen chloride or chlorine in the presence of Lewis acid catalyst under conditions sufficient to convert the by-product to organic tetravalent tin polyhalide, and, (c) recovering organic tetravalent tin polyhalide.

DESCRIPTION OF THE PREFERRED EMBODIMENTS

The invention may be further described by the following examples; but the scope of the invention is not to be limited thereby:

Reference Example 1

Synthesis of Dibutyl Tin Diiodide

In a flask (300 ml) equipped with stirrer, reflux condenser and thermometer, 41.5 g of tin foil, 200 g of butyl iodide, 3 g of butanol and 0.15 g magnesium foil were loaded and re-fluxed on a mantel heater for 2 hours. After a portion of the tin foil reacted and was consumed, the refluxing reaction condition was continued for 4 hours with stirring until the tin foil disappeared.

Excess butyl iodide was recovered by vacuum distillation and the residual solution washed by hydrochloric acid at room temperature; thus, 168 g of dibutyl tin diiodide was obtained as pale yellowish clear liquid, which composition was analyzed by chromatography (abbreviated as GC, hereafter). The analytical result showed that it was composed of 4.2% of monobutyl tetravalent tin triiodide, 92.4% of dibutyl tetravalent tin diiodide, 2.3% of tributyl tetravalent tin monoiodide and 1.1% of other by-products.

EXAMPLE 1

In a similar flask (300 ml) as Reference Example 1, 50 g of dibutyl tin diiodide obtained in the Reference Example 1 and 10 g of 35% hydrochloric acid was introduced and slowly heated to refluxing temperature of about 120° C. From a dropping funnel, 30 g of 35% hydrochloric acid was dropped into the flask for 30 minutes, and the water phase subsequently removed. Just after the reacting solution reached refluxing temperature, an evolution of hydrogen chloride from top of the reflux condenser was observed and it was recovered. Additionally, 30 g of 35% of hydrochloric acid was dropped into the flask and this procedure was repeated 5 times. The dropped total amount of hydrochloric acid was 150 g. After the reaction, the mixture was cooled at room temperature and the discarded water phase recovered by a separatory funnel. Powdery 24.9 g of dibutyl tin oxide was obtained by hydrolysis of the treated dibutyl tetravalent tin diiodide according to a method described in Example 1 of Japanese Pat. No. Sho 61-291592 (1986). Content of tributyl tin compounds in the recovered substance was analyzed by gas chromatography and found to be less than detectable limit.

EXAMPLE 2

In a similar apparatus as described Reference Example 1, equipped with a distillation condenser instead of reflux one, 50 g of dibutyl tetravalent tin diiodide obtained in the Reference Example 1 was heated at 150° C. and 30 g of 35% hydrochloric acid was slowly added while maintaining the temperature at 150–160° C. As soon as the dropping began, the reaction proceeded, the water phase boiled, and then, the water phase was distilled out. After the dropping addition was completed, the reaction mixture was cooled at room temperature and analyzed by GC. It was shown by GC analysis that the resulting mixture was composed of 4.9% of monobutyl tetravalent tin triiodide, 94.0% of dibutyl tetravalent tin diiodide, 0.6% of tributyl tetravalent tin monoiodide and 0.5% of other by-products.

Through an inserted glass tube beneath the surface of the reaction mixture in the apparatus, hydrogen chloride was blown in at 150° C. for 60 minutes. The treated dibutyl tetravalent tin diiodide was hydrolyzed as described in Example 1. It was shown by GC analysis that tributyl tetravalent tin compound in the obtained dibutyl tetravalent tin diiodide was less than detectable limit.

EXAMPLE 3

In a similar apparatus as described in Reference Example 1, equipped with a blowing tube for gas, 50 g of dibutyl tetravalent tin diiodide obtained in the Reference Example 1 was heated at 150° C. under stirring condition. Through the inserted glass tube beneath the surface of the reaction mixture in the apparatus, hydrogen chloride was blown in at the rate of 30 ml/min. while maintaining the same temperature. The reaction was continued for 120 minutes with blowing the gas. When evolution of butane gas with unreacted hydrogen chloride was observed from top of the condenser, the reaction was discontinued. After cooling the reaction mixture at room temperature, it was hydrolyzed as described in Example 1. It was shown by GC analysis that tributyl tin compound in the obtained dibutyl tin diiodide was less than detectable limit.

Reference Example 2

Dibutyl Tin Dichloride

In a similar apparatus as described in Reference Example 1, 67 g of tetrabutyl tetravalent tin, 50 g of anhydrous stannic chloride and 3 g of anhydrous aluminum chloride were reacted at 140° C. for 3 hours. After cooling at room temperature, 100 ml of 1,1,1-trichloroethane was added, and the reaction mixture was washed by two portions of 50 ml of 5% hydrochloric acid the water phase was separated to discarded. After the trichloroethane was eliminated by evaporation, then dibutyl tin dichloride was obtained as pale yellowish liquid, which was composed of 2.1% of monobutyl tetravalent tin trichloride, 94.2% of dibutyl tetravalent tin dichloride, 3.4% of tributyl tetravalent tin monochloride, and 0.3% of other by-products, according to GC analysis.

EXAMPLE 4

In a similar apparatus as described in Reference Example 1, 50 g of liquid dibutyl tetravalent tin dichloride obtained in Reference Example 2 and 40 g of 35% hydrochloric acid were heated to reflux temperature and kept at the refluxing temperature for 30 minutes. After water phase was removed from the reaction mixture, the mixture was refluxed with 40 g of 35% hydrochloric acid. The procedures were repeated 5 times. After terminating the reaction, the mixture was cooled at room temperature and the water phase was removed. Powdery 41.5 g of dibutyl tin oxide was obtained by hydrolysis of the resulted substance according to a method described in Example 3 of Japanese Pat. No. Sho 61-291592 (1986). Content of tributyl tin compound in the oxide was analyzed by gas chromatography and was less than detectable limit.

EXAMPLE 5

In a similar apparatus as described in Reference Example 2, equipped with a blowing tube for gas, 50 g of dibutyl tetravalent tin dichloride obtained in the Reference Example 2 was heated at 150° C. under stirring condition. Through the inserted glass tube beneath the surface of the reaction mixture in the apparatus, hydrogen chloride was blown in at the rate of 30 ml/min. while maintaining the same temperature for 2 hours. After cooling the reaction mixture at room temperature, it was hydrolyzed as described in Example 4. It was shown by GC analysis that tributyl tetravalent tin compound in the obtained dibutyl tetravalent tin diiodide was less than detectable limit.

EXAMPLE 6

In a similar apparatus as described in Reference Example 2, equipped with a blowing tube for gas, 50 g of dibutyl tetravalent tin dichloride obtained in the Reference Example 2, and anhydrous aluminum chloride were heated at 150° C. under stirring condition. Through the inserted glass tube beneath the surface of the reaction mixture in the apparatus, hydrogen chloride was blown in at the rate of 30ml/min. while maintaining at the same temperature for 1 hour. The reaction mixture was cooled at room temperature. It was shown by GC analysis that tributyl tetravalent tin compound in the obtained dibutyl tetravalent tin dichloride was less than detectable limit.

EXAMPLE 7

In a similar apparatus as described in Reference Example 1, equipped with a blowing tube for gas, 50 g of a monobutyl tetravalent tin trichloride mixture which is composed of 5.4% of tributyl tetravalent tin monochloride, 3.1% of dibutyl tetravalent tin dichloride, 91.2% of monobutyl tetravalent tin trichloride and 0.3% of other by-products, and 1.5 g of anhydrous aluminum chloride were heated at 150° C. under stirring condition. Through the inserted glass tube beneath the surface of the reaction mixture in the apparatus, hydrogen chloride was blown in at the rate of 30 ml/min. while maintaining the same temperature for 20 minutes. After the reaction was complete and the mixture cooled, it was shown by GC analysis that the obtained substance was composed of 2.9% of dibutyl tetravalent tin dichloride, 96.9% of monobutyl tetravalent tin trichloride, less than detectable limit (10 ppm) of tributyl tin tetravalent monochloride and 0.5% of the other by-products.

EXAMPLE 8

In a similar apparatus as described in Reference Example 2, equipped with a blowing tube for gas, 50 g of dibutyl tetravalent tin dichloride obtained in the Reference Example 2 was heated at 150° C. under stirring condition. Through the inserted glass tube beneath the surface of the reaction mixture in the apparatus, chlorine was blown in at the rate of 30 ml/min. while maintaining the same temperature for 30 minutes. After cooling the reaction mixture at room temperature, it was shown by GC analysis that tributyl tetravalent tin compound in the obtained dibutyl tetravalent tin diiodide was less than detectable limit (10 ppm).

INDUSTRIAL APPLICABILITY

In organic tin polyhalides and organic tin oxides manufactured by formerly developed industrial process, organic tin monohalide was always contaminated in the products. According to the invention, the organic tin monohalide can be eliminated from the products so that it cannot be detected in sensitivity of ordinary gas chromatography.

This invention is clearly new and useful. Moreover, it was not obvious to those of ordinary skill in the art at the time it was made, in view of the prior art when considered as a whole.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. Method for producing an organic tetravalent tin polyhalide which comprises contacting an admixture of organic tetravalent tin polyhalide and organic tetravalent tin monohalide with hydrochloric acid, hydrogen chloride or chlorine in an amount and under conditions sufficient to convert the organic tetravalent tin monohalide to organic tetravalent tin polyhalide.

2. Method according to claim 1 wherein the condition include the presence of a Lewis acid catalyst.

3. Method for producing an organic tetravalent tin polyhalide which comprises contacting an admixture of an organic tetravalent tin polyhalide of the formula $$R_2SnX_2 \quad (A)$$

wherein
R is alkyl or phenyl, and,
X is chlorine, bromine, or iodine and an organic tetravalent tin monohalide of the formula $$R_3SnX \quad (B)$$

wherein
R is alkyl or phenyl, and,
X is chlorine, bromine, or iodine
with hydrochloric acid, hydrogen chloride, or chlorine in an amount from 1 to 100 moles per mole of (B) and at a temperature from 100° to 250° C. sufficient to convert (B) to (A).

4. Method according to claim 3 wherein the contact of (A) and (B) with the hydrochloric acid, hydrogen chloride, or chlorine is in the presence of a Lewis acid catalyst selected from the group consisting of $AlCl_3$, $AlBr_3$, $AlI_3$, $GaBr_3$, $GaCl_3$, $FeCl_3$, $SbCl_3$, $SnCl_4$, $SnI_4$, $ZnCl_4$, $BCl_3$ $BF_3$, and $ZnCl_3$.

5. Method according to claim 4 wherein the Lewis acid is $AlCl_3$.

6. Method for producing an organic tetravalent tin polyhalide which comprises
    (a) the process of reacting a tetravalent tin halide with organoaluminim, a Grignard agent, or the process of reacting metallic tetravalent tin with an organohalide, thereby producing a reaction product comprising an organic tetravalent tin polyhalide and by-product organic tetravalent tin monohalide, such process does not include the removal of the by-product,
    (b) contacting the reaction product with hydrochloric acid, hydrogen chloride or chlorine in the presence of Lewis acid catalyst under conditions sufficient to convert the by-product to organic tetravalent tin polyhalide, and,
    (c) recovering organic tetravalent tin polyhalide.

7. Method according to claim 6 wherein the organic tetravalent tin polyhalide comprises compounds of the formula $$R_2SnX_2 \quad (A)$$

wherein
R is alkyl or phenyl, and,
X is chlorine, bromine, or iodine
the organic tetravalent tin monohalide by-product comprises compound of the formula $$R_3SnX \quad (B)$$

wherein
R is alkyl or phenyl, and
X is chlorine, bromine or iodine,
and, the Lewis acid is selected from the group consisting of $AlCl_3$, $AlBr_3$, $AlI_3$, $GaBr_3$, $GaCl_3$, $FeCl_3$, $SbCl_3$, $SnCl_4$, $SnI_4$, $ZrCl_4$, $BCl_3$ $BF_3$, and $ZnCl_3$.

8. Method according to claim 7 wherein the conditions of conversion include a mole ratio of 20 to 50 moles of hydrochloric acid, hydrogen chloride, or chlorine to one mole of (B), and a temperature from 100° to 200° C.

9. Method according to claim 8 wherein the Lewis acid is $AlCl_3$.

* * * * *